United States Patent
Penner

(10) Patent No.: US 8,934,972 B2
(45) Date of Patent: *Jan. 13, 2015

(54) ACOUSTICALLY POWERED IMPLANTABLE STIMULATING DEVICE

(71) Applicant: Remon Medical Technologies, Ltd., Caesarea (IL)

(72) Inventor: Abraham Penner, Tel Aviv (IL)

(73) Assignee: Remon Medical Technologies, Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/843,381

(22) Filed: Mar. 15, 2013

(65) Prior Publication Data
US 2013/0226259 A1   Aug. 29, 2013

Related U.S. Application Data

(63) Continuation of application No. 13/046,083, filed on Mar. 11, 2011, now Pat. No. 8,577,460, which is a continuation of application No. 11/871,017, filed on Oct. 11, 2007, now Pat. No. 7,930,031, which is a (Continued)

(51) Int. Cl.
*A61N 1/00* (2006.01)
*A61N 1/08* (2006.01)

(Continued)

(52) U.S. Cl.
CPC ............... *A61N 1/08* (2013.01); *A61B 5/0031* (2013.01); *A61N 1/3787* (2013.01); *A61N 1/3718* (2013.01); *A61N 7/00* (2013.01);

(Continued)

(58) Field of Classification Search
USPC ........ 128/897–899, 903–905; 607/33, 59–60, 607/11, 17, 62, 116; 600/300, 486
See application file for complete search history.

(56) References Cited

U.S. PATENT DOCUMENTS

| 2,463,533 | A | 3/1949 | Harrison |
| 2,786,899 | A | 3/1957 | Carlisle et al. |

(Continued)

FOREIGN PATENT DOCUMENTS

| EP | 0 499 939 | 8/1992 |
| EP | 0 928 598 | 12/1998 |

(Continued)

OTHER PUBLICATIONS

Harrison et al., "A Low-Power Low-Noise CMOS Amplifier for Neural Recording Applications," IEEE Journal of Solid-State Circuits 38(6):958-965, Jun. 2003.

(Continued)

*Primary Examiner* — Eric D. Bertram
*Assistant Examiner* — Elizabeth K So
(74) *Attorney, Agent, or Firm* — Faegre Baker Daniels LLP

(57) ABSTRACT

An implantable stimulation system comprises an implantable stimulator and a control device. The control device is configured to transmit acoustic waves to the implantable stimulator, and the implantable stimulator is configured to transform the acoustic waves into electrical current, and generate stimulation energy based on the electrical current. For example, the electrical current can be transformed into electrical energy that can be used to generate the stimulation energy. Or the electrical current can contain signals used to directly or indirectly control the generation of the stimulation energy.

8 Claims, 6 Drawing Sheets

Related U.S. Application Data continuation of application No. 10/632,265, filed on Jul. 31, 2003, now Pat. No. 7,283,874, which is a continuation-in-part of application No. 09/989,912, filed on Nov. 19, 2001, now Pat. No. 7,024,248, which is a continuation-in-part of application No. 09/690,615, filed on Oct. 16, 2000, now Pat. No. 6,628,989, said application No. 10/632,265 is a continuation-in-part of application No. 09/888,272, filed on Jun. 21, 2001, now Pat. No. 6,764,446, which is a continuation-in-part of application No. 09/690,615, said application No. 10/632,265 is a continuation-in-part of application No. 10/413,428, filed on Apr. 14, 2003, now Pat. No. 7,198,603.

(51) Int. Cl.

| | | |
|---|---|---|
| *A61B 5/00* | (2006.01) | |
| *A61N 1/378* | (2006.01) | |
| *A61N 1/37* | (2006.01) | |
| *A61N 7/00* | (2006.01) | |
| *A61N 1/362* | (2006.01) | |
| *A61B 17/00* | (2006.01) | |
| *A61N 1/372* | (2006.01) | |

(52) U.S. Cl.
CPC ...... *A61N 1/362* (2013.01); *A61B 2017/00026* (2013.01); *A61B 2560/0219* (2013.01); *A61B 2562/028* (2013.01); *A61N 1/37217* (2013.01)
USPC .......................................................... 607/33

(56) References Cited

U.S. PATENT DOCUMENTS

| | | |
|---|---|---|
| 3,536,836 A | 10/1970 | Pfeiffer |
| 3,672,352 A | 6/1972 | Summers |
| 3,757,770 A | 9/1973 | Brayshaw et al. |
| 3,805,796 A | 4/1974 | Terry, Jr. et al. |
| 3,853,117 A | 12/1974 | Murr |
| 3,943,915 A | 3/1976 | Severson |
| 3,970,987 A | 7/1976 | Kolm |
| 4,026,276 A | 5/1977 | Chubbuck |
| 4,041,954 A | 8/1977 | Ohara |
| 4,062,354 A | 12/1977 | Taylor et al. |
| 4,082,097 A | 4/1978 | Mann et al. |
| 4,099,530 A | 7/1978 | Chen et al. |
| 4,127,110 A | 11/1978 | Bullara |
| 4,170,742 A | 10/1979 | Itagaki et al. |
| 4,206,761 A | 6/1980 | Cosman |
| 4,206,762 A | 6/1980 | Cosman |
| 4,265,252 A | 5/1981 | Chubbuck et al. |
| 4,281,666 A | 8/1981 | Cosman |
| 4,281,667 A | 8/1981 | Cosman |
| 4,340,038 A | 7/1982 | Mc Kean |
| 4,354,506 A | 10/1982 | Sakaguchi et al. |
| 4,361,153 A | 11/1982 | Slocum et al. |
| 4,378,809 A | 4/1983 | Cosman |
| 4,385,636 A | 5/1983 | Cosman |
| 4,407,296 A | 10/1983 | Anderson |
| 4,471,786 A | 9/1984 | Inagaki et al. |
| 4,481,950 A | 11/1984 | Duggan |
| 4,494,950 A | 1/1985 | Fischell |
| 4,519,401 A | 5/1985 | Ko et al. |
| 4,556,061 A | 12/1985 | Barreras et al. |
| 4,593,703 A | 6/1986 | Cosman |
| 4,596,255 A | 6/1986 | Snell et al. |
| 4,614,192 A | 9/1986 | Imran et al. |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,708,127 A | 11/1987 | Abdelghani |
| 4,719,919 A | 1/1988 | Christopher et al. |
| 4,791,915 A | 12/1988 | Barsotti et al. |
| 4,791,936 A | 12/1988 | Snell et al. |
| 4,793,825 A | 12/1988 | Benjamin et al. |
| 4,869,251 A | 9/1989 | Lekholm et al. |
| 4,885,002 A | 12/1989 | Watanabe et al. |
| 4,886,065 A | 12/1989 | Collings, Jr. |
| 4,911,217 A | 3/1990 | Dunn et al. |
| 4,918,736 A | 4/1990 | Bordewijk |
| 5,074,310 A | 12/1991 | Mick |
| 5,113,859 A | 5/1992 | Funke |
| 5,117,835 A | 6/1992 | Mick |
| 5,160,870 A | 11/1992 | Carson et al. |
| 5,168,869 A | 12/1992 | Chirife |
| 5,184,605 A | 2/1993 | Grzeszykowski |
| 5,218,861 A | 6/1993 | Brown et al. |
| 5,279,292 A | 1/1994 | Baumann et al. |
| 5,291,899 A | 3/1994 | Watanabe et al. |
| 5,381,067 A | 1/1995 | Greenstein et al. |
| 5,423,334 A | 6/1995 | Jordan |
| 5,433,736 A | 7/1995 | Nilsson |
| 5,438,554 A | 8/1995 | Seyed-Bolorforosh et al. |
| 5,445,150 A | 8/1995 | Dumoulin et al. |
| 5,495,453 A | 2/1996 | Wociechowski et al. |
| 5,562,621 A | 10/1996 | Claude et al. |
| 5,619,997 A | 4/1997 | Kaplan |
| 5,620,475 A | 4/1997 | Magnusson |
| 5,704,352 A | 1/1998 | Tremblay et al. |
| 5,704,366 A | 1/1998 | Tacklind et al. |
| 5,712,917 A | 1/1998 | Offutt |
| 5,721,886 A | 2/1998 | Miller |
| 5,724,985 A | 3/1998 | Snell et al. |
| 5,733,249 A | 3/1998 | Katzin et al. |
| 5,743,267 A | 4/1998 | Nikolic et al. |
| 5,749,909 A | 5/1998 | Schroeppel et al. |
| 5,757,104 A | 5/1998 | Getman et al. |
| 5,759,199 A | 6/1998 | Snell et al. |
| 5,776,168 A | 7/1998 | Gunderson |
| 5,800,478 A | 9/1998 | Chen et al. |
| 5,807,258 A | 9/1998 | Cimochowski et al. |
| 5,814,089 A | 9/1998 | Stokes et al. |
| 5,833,603 A | 11/1998 | Kovacs et al. |
| 5,861,018 A | 1/1999 | Feierbach |
| 5,876,353 A | 3/1999 | Riff |
| 5,891,180 A | 4/1999 | Greeninger et al. |
| 5,904,708 A | 5/1999 | Goedeke |
| 5,925,001 A | 7/1999 | Hoyt et al. |
| 5,935,078 A | 8/1999 | Feierbach |
| 5,957,861 A | 9/1999 | Combs et al. |
| 5,967,989 A | 10/1999 | Cimochowski et al. |
| 6,015,387 A | 1/2000 | Schwartz et al. |
| 6,030,374 A | 2/2000 | McDaniel |
| 6,070,103 A | 5/2000 | Ogden |
| 6,140,740 A | 10/2000 | Porat et al. |
| 6,141,588 A | 10/2000 | Cox |
| 6,162,238 A | 12/2000 | Kaplan et al. |
| 6,164,284 A | 12/2000 | Schulman et al. |
| 6,167,303 A | 12/2000 | Thompson |
| 6,170,488 B1 | 1/2001 | Spillman, Jr. et al. |
| 6,176,840 B1 | 1/2001 | Nishimura et al. |
| 6,183,426 B1 | 2/2001 | Akisada et al. |
| 6,185,452 B1 | 2/2001 | Schulman et al. |
| 6,185,454 B1 | 2/2001 | Thompson |
| 6,185,460 B1 | 2/2001 | Thompson |
| 6,198,963 B1 | 3/2001 | Haim et al. |
| 6,198,965 B1 | 3/2001 | Penner et al. |
| 6,198,971 B1 | 3/2001 | Leysieffer |
| 6,200,265 B1 | 3/2001 | Walsh et al. |
| 6,236,889 B1 | 5/2001 | Soykan et al. |
| 6,237,398 B1 | 5/2001 | Porat et al. |
| 6,248,080 B1 | 6/2001 | Miesel et al. |
| 6,259,951 B1 | 7/2001 | Kuzma et al. |
| 6,260,152 B1 | 7/2001 | Cole et al. |
| 6,261,249 B1 | 7/2001 | Tallish et al. |
| 6,277,078 B1 | 8/2001 | Porat et al. |
| 6,315,721 B2 | 11/2001 | Schulman et al. |
| 6,427,088 B1 | 7/2002 | Bowman et al. |
| 6,431,175 B1 | 8/2002 | Penner et al. |

(56) References Cited

U.S. PATENT DOCUMENTS

| | | |
|---|---|---|
| 6,432,050 B1 | 8/2002 | Porat et al. |
| 6,442,413 B1 | 8/2002 | Silver |
| 6,442,433 B1 | 8/2002 | Linberg |
| 6,472,991 B1 | 10/2002 | Schulman et al. |
| 6,473,638 B2 | 10/2002 | Ferek-Petric |
| 6,564,807 B1 | 5/2003 | Schulman et al. |
| 6,577,899 B2 | 6/2003 | Lebel et al. |
| 6,584,352 B2 | 6/2003 | Combs et al. |
| 6,607,485 B2 | 8/2003 | Bardy |
| 6,628,989 B1 | 9/2003 | Penner et al. |
| 6,644,322 B2 | 11/2003 | Webb |
| 6,664,763 B2 | 12/2003 | Echarri et al. |
| 6,671,552 B2 | 12/2003 | Merritt et al. |
| 6,676,601 B1 | 1/2004 | Lacoste |
| 6,689,091 B2 | 2/2004 | Bui et al. |
| 6,712,772 B2 | 3/2004 | Cohen et al. |
| 6,731,976 B2 | 5/2004 | Penn et al. |
| 6,735,532 B2 | 5/2004 | Freed et al. |
| 6,754,538 B2 | 6/2004 | Linberg |
| 6,764,446 B2 | 7/2004 | Wolinsky et al. |
| 6,788,973 B2 | 9/2004 | Davis et al. |
| 6,790,187 B2 | 9/2004 | Thompson et al. |
| 6,799,280 B1 | 9/2004 | Edenfield et al. |
| 6,804,557 B1 | 10/2004 | Kroll |
| 6,826,430 B2 | 11/2004 | Faltys et al. |
| 6,855,115 B2 | 2/2005 | Fonseca et al. |
| 6,873,869 B2 | 3/2005 | Fischer |
| 6,960,801 B2 | 11/2005 | Lung |
| 6,970,037 B2 | 11/2005 | Sakhuja et al. |
| 6,978,181 B1 | 12/2005 | Snell |
| 6,985,088 B2 | 1/2006 | Goetz et al. |
| 6,985,773 B2 | 1/2006 | Von Arx et al. |
| 6,988,215 B2 | 1/2006 | Splett et al. |
| 6,993,393 B2 | 1/2006 | Von Arx et al. |
| 7,003,349 B1 | 2/2006 | Andersson et al. |
| 7,013,178 B2 | 3/2006 | Reinke et al. |
| 7,024,248 B2 | 4/2006 | Penner et al. |
| 7,027,871 B2 | 4/2006 | Burnes et al. |
| 7,027,872 B2 | 4/2006 | Thompson |
| 7,035,684 B2 | 4/2006 | Lee |
| 7,060,030 B2 | 6/2006 | Von Arx et al. |
| 7,061,381 B2 | 6/2006 | Forcier et al. |
| 7,082,334 B2 | 7/2006 | Boute et al. |
| 7,096,068 B2 | 8/2006 | Mass et al. |
| 7,123,964 B2 | 10/2006 | Betzold et al. |
| 7,198,603 B2 | 4/2007 | Penner et al. |
| 7,203,551 B2 | 4/2007 | Houben et al. |
| 7,209,790 B2 | 4/2007 | Thompson et al. |
| 7,212,133 B2 | 5/2007 | Goetz et al. |
| 7,236,821 B2 | 6/2007 | Cates et al. |
| 7,273,457 B2 | 9/2007 | Penner et al. |
| 7,283,874 B2 | 10/2007 | Penner et al. |
| 7,286,872 B2 | 10/2007 | Kramer et al. |
| 7,319,903 B2 | 1/2008 | Bange et al. |
| 7,335,161 B2 | 2/2008 | Von Arx et al. |
| 7,353,063 B2 | 4/2008 | Simms, Jr. |
| 7,469,161 B1 | 12/2008 | Gandhi et al. |
| 7,479,108 B2 | 1/2009 | Rini et al. |
| 7,617,001 B2 | 11/2009 | Penner et al. |
| 7,650,185 B2 | 1/2010 | Maile et al. |
| 7,756,587 B2 | 7/2010 | Penner et al. |
| 7,930,031 B2 | 4/2011 | Penner |
| RE42,378 E | 5/2011 | Wolinsky et al. |
| 8,078,278 B2 | 12/2011 | Penner |
| 8,271,093 B2 | 9/2012 | Von Arx et al. |
| 8,340,776 B2 | 12/2012 | Doron et al. |
| 8,374,693 B2 | 2/2013 | Chavan et al. |
| 2001/0025139 A1 | 9/2001 | Pearlman |
| 2002/0065540 A1 | 5/2002 | Lebel et al. |
| 2002/0077673 A1 | 6/2002 | Penner et al. |
| 2002/0151770 A1 | 10/2002 | Noll, III et al. |
| 2002/0169584 A1 | 11/2002 | Fu et al. |
| 2003/0114897 A1 | 6/2003 | Von Arx et al. |
| 2003/0212441 A1 | 11/2003 | Starkweather et al. |
| 2004/0039424 A1 | 2/2004 | Merritt et al. |
| 2004/0133092 A1 | 7/2004 | Kain |
| 2004/0152999 A1 | 8/2004 | Cohen et al. |
| 2004/0172083 A1 | 9/2004 | Penner |
| 2004/0210141 A1 | 10/2004 | Miller |
| 2005/0109338 A1 | 5/2005 | Stahmann et al. |
| 2005/0113705 A1 | 5/2005 | Fischell et al. |
| 2005/0136385 A1 | 6/2005 | Mann et al. |
| 2005/0159785 A1 | 7/2005 | Rueter |
| 2005/0159789 A1 | 7/2005 | Brockway et al. |
| 2005/0177135 A1 | 8/2005 | Hildebrand et al. |
| 2005/0182387 A1 | 8/2005 | Webler |
| 2005/0203444 A1 | 9/2005 | Schonenberger et al. |
| 2005/0265999 A1 | 12/2005 | Bush et al. |
| 2005/0288727 A1 | 12/2005 | Penner |
| 2006/0009818 A1 | 1/2006 | Von Arx et al. |
| 2006/0020307 A1 | 1/2006 | Davis et al. |
| 2006/0025834 A1 | 2/2006 | Von Arx et al. |
| 2006/0031378 A1 | 2/2006 | Vallapureddy et al. |
| 2006/0041287 A1 | 2/2006 | Dewing et al. |
| 2006/0041288 A1 | 2/2006 | Dewing et al. |
| 2006/0058627 A1 | 3/2006 | Flaherty et al. |
| 2006/0064134 A1 | 3/2006 | Mazar et al. |
| 2006/0064135 A1 | 3/2006 | Brockway |
| 2006/0064142 A1 | 3/2006 | Chavan et al. |
| 2006/0085039 A1 | 4/2006 | Hastings et al. |
| 2006/0094967 A1 | 5/2006 | Bennett et al. |
| 2006/0122667 A1 | 6/2006 | Chavan et al. |
| 2006/0142819 A1 | 6/2006 | Penner et al. |
| 2006/0149329 A1 | 7/2006 | Penner |
| 2007/0010742 A1 | 1/2007 | Torp et al. |
| 2007/0055317 A1 | 3/2007 | Strahmann et al. |
| 2007/0142728 A1 | 6/2007 | Penner et al. |
| 2007/0150014 A1 | 6/2007 | Kramer et al. |
| 2007/0162090 A1 | 7/2007 | Penner |
| 2007/0179549 A1 | 8/2007 | Russie |
| 2007/0250126 A1 | 10/2007 | Maile et al. |
| 2008/0015421 A1 | 1/2008 | Penner |
| 2008/0071178 A1 | 3/2008 | Greenland et al. |
| 2008/0103553 A1 | 5/2008 | Penner et al. |
| 2008/0108915 A1 | 5/2008 | Penner |
| 2008/0171941 A1 | 7/2008 | Huelskamp et al. |
| 2008/0195002 A1 | 8/2008 | Thompson et al. |
| 2008/0228094 A1 | 9/2008 | Audet et al. |
| 2008/0243007 A1 | 10/2008 | Liao et al. |
| 2008/0243210 A1 | 10/2008 | Doron et al. |
| 2009/0312650 A1 | 12/2009 | Maile et al. |
| 2009/0326609 A1 | 12/2009 | Doron |
| 2010/0023091 A1 | 1/2010 | Stahmann et al. |
| 2010/0106028 A1 | 4/2010 | Penner et al. |
| 2010/0274302 A1 | 10/2010 | Armstrong et al. |
| 2011/0160804 A1 | 6/2011 | Penner |
| 2013/0218251 A1 | 8/2013 | Penner |
| 2013/0238044 A1 | 9/2013 | Penner |

FOREIGN PATENT DOCUMENTS

| | | |
|---|---|---|
| EP | 1 962 557 | 8/2008 |
| JP | 05-023323 | 2/1993 |
| JP | 08-331065 | 12/1996 |
| JP | 09-147284 | 6/1997 |
| JP | 10-093477 | 4/1998 |
| JP | 10-505529 | 6/1998 |
| JP | 2002-515807 | 5/2002 |
| JP | 2002515807 A | 5/2002 |
| JP | 2004-041724 | 2/2004 |
| JP | 2004041724 A | 2/2004 |
| JP | 2004-511313 | 4/2004 |
| JP | 2004-537347 | 12/2004 |
| JP | 2005-521528 | 7/2005 |
| WO | WO 88/02250 | 4/1988 |
| WO | WO 96/26673 | 9/1996 |
| WO | WO 97-33513 | 9/1997 |
| WO | WO 98/43338 | 10/1998 |
| WO | WO 98/43701 | 10/1998 |
| WO | WO 98-52142 | 11/1998 |
| WO | WO 99-04287 | 1/1999 |
| WO | WO 99/34453 | 7/1999 |
| WO | WO 00/47109 | 8/2000 |
| WO | WO 01/28627 | 4/2001 |

(56) References Cited

FOREIGN PATENT DOCUMENTS

| WO | WO 01/74278 | 10/2001 |
|---|---|---|
| WO | WO 01/76687 | 10/2001 |
| WO | WO 01/97907 | 12/2001 |
| WO | WO 02/03347 | 1/2002 |
| WO | WO 02/32502 | 4/2002 |
| WO | WO 02/089904 | 11/2002 |
| WO | WO 03/002243 | 1/2003 |
| WO | WO 03/043688 | 5/2003 |
| WO | WO 03/096889 | 11/2003 |
| WO | WO 2004/089465 | 10/2004 |
| WO | WO 2005/009535 | 2/2005 |
| WO | WO 2005/053786 | 6/2005 |
| WO | WO 2005/099816 | 10/2005 |
| WO | WO 2006/017615 | 2/2006 |
| WO | WO 2006034183 | 3/2006 |
| WO | WO 2006/060668 | 6/2006 |
| WO | WO 2006/126401 | 11/2006 |
| WO | WO 2007/070794 | 6/2007 |
| WO | WO 2007/080487 | 7/2007 |
| WO | WO 2007/127696 | 11/2007 |
| WO | WO 2008/118908 | 10/2008 |
| WO | WO 2010/062538 | 6/2010 |

OTHER PUBLICATIONS

IEEE Transactions on Biomedical Engineering, vol. 42, No. 5, May 1995, Title: Data Transmission from an Implantable Biotelemeter by Load-Shift Keying Using Circuit Configuration Modulator, by Zhengnian Tang, Brian Smith, John H. Schild, and P. Hunter Peckham, pp. 524-528.

Ishiwara et al., "Current Status and Prospects of FET-Type Ferroelectric Memories," Journal of Semiconductor Technology and Science 1(1): 1-14, Mar. 2001.

Neurosurgery Clinics of North America vol. 4, No. 4, Oct. 1993, Hydrocephalus, Title: The Treatment of Hydrocephalus by Paul M. Kanev, MD, and T.S. Park, MD., pp. 611-619.

Neurosurgery Clinics of North America, vol. 4, No. 4, Oct. 1993, Hydrocephalus, Title: Complications in Ventricular Cerebrospinal Fluid Shunting by Jeffrey P. Blount, MD, John A. Campbell, MD, and Stephen J. Haines, MD, pp. 633-656.

Neurosurgery Update II Vascular, Spinal, Pediatric, and Functional Neurosurgery, Published by McGraw-Hill, Inc., 1991, Editors Robert H. Wilkins, M.D., and Setti S. Rengachary, M.D., Title Shunt Complications by R. Michael Scott, pp. 300-319.

Neurosurgery, vol. 34, No. 5, May 1994, Concepts and Innovations, Title: A New Ventricular Catheter for the Prevention and Treatment of Proximal Obstruction in Cerebrospinal Fluid Shunts, by Enrique C.G. Ventureyra, M.D., F.R.C.S.(C)., F.A.C.S., Michael J. Higgins, M.D., pp. 924-926.

Neurosurgery, vol. 34, No. 6, Jun. 1994, Rapid Communication, Title: The Use of the Codman-Medos Programmable Hakim Valve in the Management of Patients with Hydroceplhalus: Illustrative Cases, by Peter McL. Black, M.D., Ph.D., Rodolfo Hakim, M.D., Nancy Olsen Bailey, R.N., B.S.N., M.B.A., pp. 1110-1113.

Pediatric Neurosurgery 2nd Edition, Surgery of the Developing Nervous System, Published by W.B. Saunders Company Harcourt Brace Jovanovich, Inc., 1989. Title: Treatment of Hydrocephalus by Harold L. Rekate, M.D.; Ventricular Shunts: Complications and Results by Robert L. McLaurin, M.D.; pp. 200-229.

International Search Report and Written Opinion issued in PCT/US2009/062019, 14 pages, Dec. 4, 2010.

Extended European Search Report issued in EP 10184174, mailed Dec. 7, 2010.

U.S. Appl. No. 12/427,312, Non-Final Office Action dated Dec. 4, 2013, 14 pages.

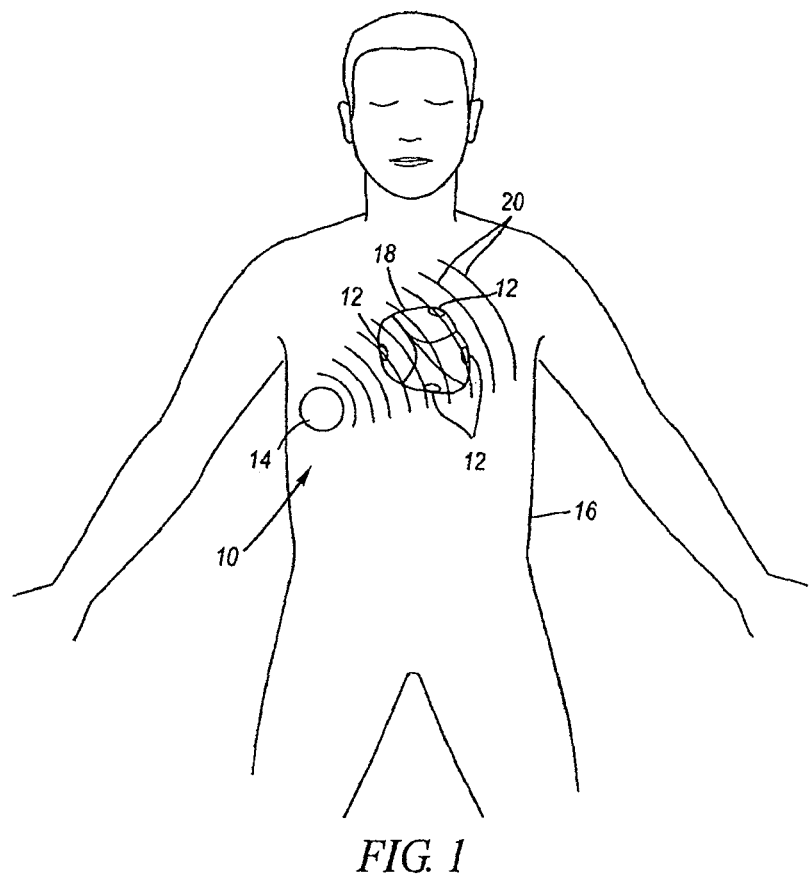
FIG. 1
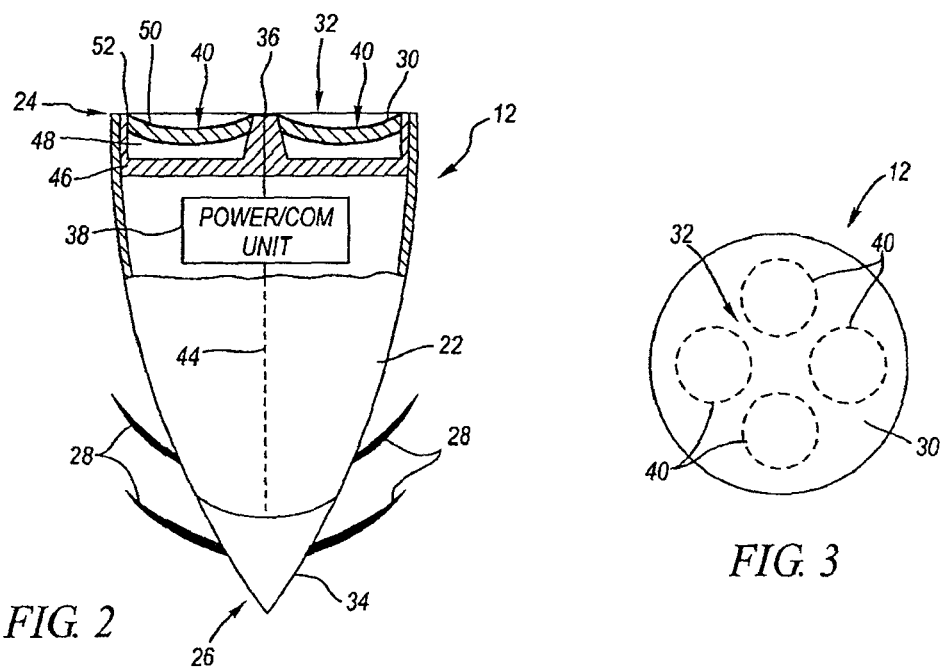
FIG. 2
FIG. 3

ACOUSTICALLY POWERED IMPLANTABLE STIMULATING DEVICE

CROSS-REFERENCE TO RELATED APPLICATIONS

This application is a continuation of co-pending U.S. application Ser. No. 13/046,083, filed Mar. 11, 2011 (now U.S. Pat.No. 8,577,460 ), which is a continuation of U.S. application Ser. No. 11/871,017, filed Oct. 11,2007 (now U.S. Pat. No. 7,930,031), which is a continuation of U.S. application Ser. No. 10/632,265, filed Jul. 31, 2003 (now U.S. Pat. No. 7,283,874), which is a (1) a continuation-in-part of U.S. application Ser. No. 09/989,912, filed Nov. 19, 2001 (now U.S. Pat. No. 7,024,248), which is a continuation-in-part of U.S. application Ser. No. 09/690,615, filed Oct. 16, 2000 (now U.S. Pat. No. 6,628,989); (2) a continuation-in-part of U.S. application Ser. No. 09/888,272, filed Jun. 21, 2001 (now U.S. Pat. No. 6,764,446), which is a continuation-in-part of U.S. application Ser. No. 09/690,615, filed Oct. 16, 2000 (now U.S. Pat. No. 6,628,989); and (3) a continuation-in-part of U.S. Pat. application Ser. No. 10/413,428, filed Apr. 14, 2003 (now U.S. Pat. No. 7,198,603). All of these applications are expressly incorporated herein by reference in their entirety for all purposes.

TECHNICAL FIELD

The present invention relates generally to medical devices for implantation within a patient's body.

BACKGROUND

Since the introduction of the heart rhythm control system—first as an implantable pacemaker in the 1960's, and then as an implantable defibrillator in 1980, implantable electrical stimulating devices have been developed to treat various medical diseases and physiological ailments, such as chronic pain disorders (e.g., nerve injury, failed back syndrome, intractable facial pain, failed neck syndrome, reflex sympathetic dystrophy, thoracic outlet syndrome, and cancer), neurological disorders (e.g., intractable epilepsy and Parkinson's disease), motor disorders (e.g., spasticity, dystonia, spasmodic torticollis, athetosis, head injury, spinal cord injury, stroke, multiple sclerosis, and cerebral palsy), cardiac rhythm disorders (e.g., tachycardia and bradycardia), and psychosomatic disorders (e.g. depression and eating disorders).

Some of these implantable devices are currently being marketed. For example, implantable spinal cord stimulators are currently being used in patients to relieve pain in various parts of the body, e.g., chronic back and leg pain, cancer pain, postoperative spinal cord injury pain, and reflex sympathetic dystrophy pain. The implantation process involves placing leads in the epidural space of the spinal canal in a location that corresponds to the patient's zone of pain. A pulse generator is then implanted in the lower anterior abdominal wall and then connected to electrodes on the leads via an extension that is percutaneously routed from the pulse generator to the leads. Once the system is fully implanted, the pulse generator can then be operated to provide low-voltage electrical stimulation of the spinal cord via the leads.

Another means for managing pain involves implanting micro-current electrical neuromuscular stimulators (MENS) within a patient in the area of the perceived pain. These devices use a very low current (typically 1-100 µA) and operate on a cellular level to speed the healing process, thereby reducing pain. These devices have been specifically used to treat arthritic conditions, sports injuries, low back pain, carpal tunnel, tennis elbow, migraines and other disorders.

A stimulation system similar to the spinal cord stimulator described above is currently being used to treat Parkinson's Disease. In this application, a lead is surgically implanted into the patient's brain adjacent the subthalamic nucleus (STN) or globus pallidus internal (GPi), which control the involuntary movement symptomatic of Parkinson's Disease. A pulse generator is implanted in the patient's chest near the collarbone, and then connected to electrodes on the lead via an extension that percutaneously runs from the pulse generator to the lead. The pulse generator can then be operated to electrically stimulate the effected regions of the brain in order to block the signals that cause the disabling motor symptoms.

Pacemakers are used to alter the heart rate of a patient. A pacemaker, like the previously described devices, includes a pulse generator and leads. The pulse generator is implanted in a sub-dermal pocket in the patient chest, while the leads are inserted into a vein underneath the collar bone and threaded into the heart. Depending on the specific medical problem, a pacemaker can replace the S-A node signals that are delayed or get lost in the electrical pathway between the upper and lower heart. A pacemaker can also maintain a normal timing sequence between the upper and lower heart, and make sure that the critical lower chambers of the heart contract at an adequate rate. A pacemaker can pace a single chamber or two chambers of the right side of the heart, or even synchronize the two ventricles for optimizing the heart pumping capability.

Other electrical stimulating devices might include peripheral nerve stimulators, medical delivery or activation systems, pumps for supporting a failing heart, controlling incontinence, or controlling the opening of a body passage, such as in a shunt for treating hydrocephalus.

All of the above-described devices provide power to the pulse generator in one of two ways: installing a battery within the pulse generator or transmitting wireless energy to the generator, e.g., by wirelessly transmitting power from an external transmitter via radio frequency (RF) telemetry to an internal sub-dermal receiver hard-wired to the pulse generator. In some cases, the pulse generators may be wirelessly controlled by an external command, for example, to obtain data, and/or to activate or otherwise control the pulse generator. For those devices that use a battery, the size of the battery required to support the operational life of the device prevents the pulse generator from being located adjacent the stimulated region. As a result, the pulse generator is usually located in the body remote from electrodes, and a lead must be used to connect the generator and electrodes. For those devices that wirelessly supply power or data to the generator, RF energy may only penetrate a few millimeters into a body, because of the body's dielectric nature. Thus, RF energy may not be able to provide power to, or otherwise communicate with, an implant that is located deep within the body.

Regardless of the means used to supply power to the pulse generator, it is sometimes possible to feel the pulse generator under the skin and visually notice a slight deformity of the skin region that covers the generator. In addition, the requirement of a lead adds complexity to the medical procedure and increases the risk of infection, and in the case of pacemakers and spinal cord stimulators, increases the risk of damaging heart valves that are crossed by the lead or the spinal cord over which the lead is routed. In some cases, the electrodes may become destabilized due to the forces applied on them by the lead. In addition, the leads are typically composed of metal formed as a coil in which electrical current may be adversely induced in the presence of a strong magnetic field, such as that created during Magnetic Resonance Imaging (MRI). As a result, those patients in which these leads are implanted cannot undergo an MRI.

SUMMARY

In accordance with a first aspect of the present invention, an implantable stimulator is provided. The implantable stimulator comprises one or more acoustic transducers that are configured to transform acoustic waves into electrical current. The acoustic transducers can comprise any material capable of transforming acoustic energy into electrical energy, but in the preferred embodiment, a piezoelectric material is used. In the preferred embodiment, an array of acoustic transducers are used to maximize the received energy. The implantable stimulator further comprises a stimulating electrode configured to output stimulation energy to adjacent tissue. For example, the tissue can be heart tissue, in which case, the implantable stimulator may be a pacemaker or other cardiac therapeutic device, or the tissue can be nerve tissue, in which case, the implantable stimulator may be a neurostimulator. Other therapeutic devices are also contemplated by the present invention. The stimulation energy is based on the electrical current resulting from the transformation in the acoustic transducers. For example, the energy of the electrical current can be used to generate the stimulation energy and/or signals within the electrical current can be used to define the characteristics of the stimulation energy.

Although the present invention should not be so limited in its broadest aspects, the use of low-frequency acoustic energy (e.g., around 40 KHz) to energize and communicate with the implantable stimulator allows the stimulator to be implanted deep within the tissue of a patient.

In one preferred embodiment, the implantable stimulator comprises an energy storage device configured for storing the electrical current as electrical energy. In this case, the stored electrical energy can be subsequently used to generate stimulation energy under control of the implantable stimulator or another control device. The implantable stimulator may also comprise a switch configured for selectively outputting the electrical energy from the energy storage device to alternately activate and deactivate the implantable stimulator. In this manner, the implantable stimulator can be placed in a "dormant mode" when not in operation in order to conserve energy, and placed in an "active mode" when operated.

In one preferred embodiment, the implantable stimulator comprises control circuitry configured to control the stimulation energy output from the stimulation electrode. For example, the control circuitry can generate and output the stimulation energy or alternately open and close a switch to generate the stimulation energy. Memory can be provided for storing stimulation parameters, which can be used by the control circuitry to control the stimulation energy output from the stimulation electrode.

In another preferred embodiment, the implantable stimulator can be a "dumb device" in that it lacks control circuitry. In this case, the stimulation energy can be generated in response to the electrical current. For example, the electrical current can contain communication signals that alternately open and close a switch in order to generate the stimulation energy. Or the electrical current can be directly transformed into the stimulation energy.

In accordance with a second aspect of the present invention, a self-contained implantable stimulator is provided. The implantable stimulator comprises a casing that integrates the previously described acoustic transducers, stimulator electrode, and control circuitry. In this manner, external leads are not required, since all components necessary to generate the stimulation energy are provided in the casing.

In accordance with a third aspect of the present invention, a stimulation system is provided. The stimulation system comprises a control device configured for transmitting acoustic waves through tissue. The control device can be an external device that can be applied to the skin of the patient or worn by the patient. Or the control device can be an implantable device. In the latter case, the implantable control device may be advantageously charged by an external device using acoustic or radio frequency (RF) energy.

The stimulation system further comprises at least one implantable stimulator configured for transforming the acoustic waves into electrical current, and outputting stimulation energy to adjacent tissue, e.g., heart or nerve tissue. The implantable stimulator(s) can be configured to control the stimulation energy output from the implantable stimulator, in which case, stimulation parameters used to control the stimulation energy can be stored in the implantable stimulator. The controller can alternatively be configured to directly control the stimulation energy output from the implantable stimulator.

In one preferred embodiment, the implantable stimulator(s) is configured for storing the electrical current as electrical energy. The control device may be configured for transmitting other acoustic waves through the tissue to alternately activate and deactivate the implantable stimulator(s). If a plurality of implantable stimulators is provided, each stimulator can be assigned a unique identification code, so that the control device can specifically address the implantable stimulators. For example, the use of unique identification codes may be particularly useful when the timing of the stimulation amongst the implantable stimulators must be coordinated.

In another preferred embodiment, the implantable stimulator(s) is configured for transmitting diagnostic information to the control device, and the control device is configured for controlling the stimulation energy output from the implantable stimulator(s) based on these acoustic waves. For example, if the implantable stimulator(s) is configured for stimulating heart tissue (e.g., in the case of a pacemaker or implantable cardioverter defibrillator (ICD)), the diagnostic information can be pressure information indicative of blood flow, in which case the heart tissue can be stimulated based on this pressure information.

Other objects and features of the present invention will become apparent from consideration of the following description taken in conjunction with the accompanying drawings.

BRIEF DESCRIPTION OF THE DRAWINGS

The drawings illustrate the design and utility of preferred embodiment(s) of the present invention, in which similar elements are referred to by common reference numerals. In order to better appreciate the advantages and objects of the present invention, reference should be made to the accompanying drawings that illustrate the preferred embodiment(s). The drawings depict only an embodiment(s) of the invention, and should not be taken as limiting its scope. With this caveat, the preferred embodiment(s) will be described and explained with additional specificity and detail through the use of the accompanying drawings in which:

FIG. 1 is a plan view of an acoustic stimulation system constructed in accordance with a preferred embodiment of the present invention, particularly showing its use within a patient;

FIG. 2 is a partially cut-away side view of an implantable stimulator used in the acoustic stimulation system of FIG. 1;

FIG. 3 is a top view of the implantable stimulator of FIG. 2;

DETAILED DESCRIPTION

Figure 4:
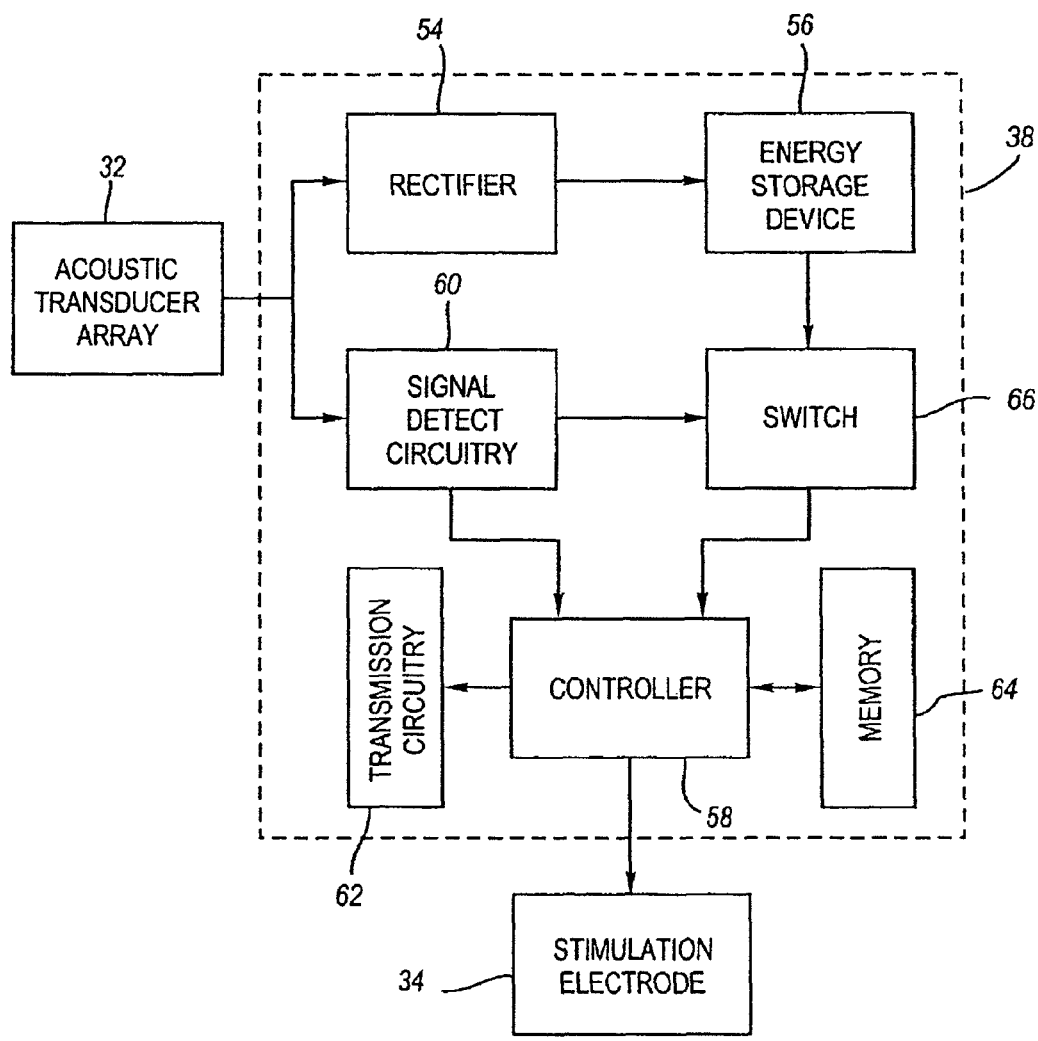
FIG. 4 is a block diagram of a preferred power/communication unit that can be used in the implantable stimulator of FIG. 2.

Referring to FIG. 1, an acoustic stimulating system 10 constructed in accordance with one preferred embodiment of the present invention is described. The stimulating system 10 generally comprises a plurality of implantable stimulators 12, which in this embodiment, take the form of pacemakers implanted within the heart 18 of a patient 16. The implantable stimulators 12 are implanted within the heart 18 using minimally invasive means, e.g., a catheter. The stimulating system 10 further comprises a control device 14 configured for being placed on the skin of the patient 16 in order to acoustically transmit acoustic waves 20 through the tissue of the patient 16 to the implantable stimulators 12. In the illustrated embodiment, the acoustic waves 20 can either be acoustic energizing waves or acoustic communication waves, as will be discussed in further detail below. Although, in the illustrated embodiment, the control device 14 is disclosed as an external device, an implantable control device can also be used to transmit acoustic waves 20 to the implantable stimulators 12, as will be described in further detail below.

The acoustic waves 20 transmitted by the control device 14 have a low frequency (e.g., 40 KHz). As such, the implantable stimulators 12 can be implanted within the deep tissue (such as the heart in this case) of the patient 16 without the need to route and implant leads within the body, thereby avoiding, or at least minimizing, the previously described complications. That is, all of the components necessary to stimulate tissue over the lifetime of the implantable stimulators 12 are contained within the implantable stimulators 12.

The control device 14 is configured to energize the implantable stimulators 12, so that the implantable stimulators 12 may subsequently or immediately output stimulation energy into the heart tissue. Besides energizing the implantable stimulators 12, the control device 14 is also configured to control the operation and configuration of the implantable stimulators 12. For example, the control device 14 may activate and deactivate implantable stimulators 12 (i.e., alternately placing them in an "active mode" and "dormant mode"). The control device 14 may also control the parameters of the stimulation energy (e.g., stimulation intensity, pulse duration, and frequency) output from any of the implantable stimulators 12. Significantly, many cardiac applications require that different regions of the heart be stimulated in a particular sequence and delay between stimulations. For example, the two ventricles of the heart may need to be synchronized to optimize the heart pumping capability. As such, the control device 14 may also control the stimulation sequence and timing of the implantable stimulators 12 to achieve this goal.

The control device 14 can selectively communicate with the implantable stimulators 12 by assigning a unique identification code to each implantable stimulator 12. Thus, the control device 14 can selectively energize or communicate with a specific implantable stimulator 12 by incorporating a corresponding unique identification code into the signal transmitted from the control device 14, or alternatively, by transmitting a predetermined pulse sequence representing the identification code prior to energizing or communicating with the specified implantable stimulator 12. By the same token, a specific implantable stimulator 12 can identify itself to the control device 14 by incorporating its unique identification code into the signal transmitting from the control device 14 or by transmitting a pulse sequence representing the unique identification code.

The stimulating system 10 can be designed in a number of manners. For example, in the preferred embodiment, the control device 14 transmits acoustic energizing waves to an implantable stimulator 14, which transforms the acoustic waves into electrical current that are then stored as electrical energy. The implantable stimulator 12 is designed with control logic, in which case, the control device 14 need only transmit stimulation parameters in the form of acoustic communication waves to program the control logic within the implantable stimulator 12, or alternatively, the implantable stimulator 12 can be preprogrammed with the stimulation parameters. The control logic will then control the stimulation energy output from the implantable stimulator 12 in accordance with these programmed stimulation parameters. For example, the control logic can, itself, generate and output the stimulation energy, or the control logic can alternately open and close a switch that selectively outputs the stored electrical energy as stimulation energy.

As another example, the control device 14 may transmit acoustic energizing waves to the implantable stimulator 12, which are then transformed into electrical energy that is immediately used to generate the stimulation energy. In this case, the control logic transforms the electrical energy into stimulation energy in accordance with stimulation parameters stored in the implantable stimulator 12. As still another example, the control device 14 may transmit acoustic energizing waves in accordance with stimulation parameters stored in the control device 14, in which case, the resulting electrical current in the implantable stimulator 12 are immediately output from the implantable stimulator 12 as stimulation energy. In the later case, the electrical current may be further processed in order to generate stimulation energy that is suitable for the intended therapy. The key here is that no energy storage device is required, since the stimulation energy is immediately output in response to the electrical current.

As still another example, the control device 14 may transmit a series of acoustic communication waves in accordance with stimulation parameters stored in the control device 14. The implantable stimulator 12 transforms the acoustic waves into electrical current that alternately open and close a switch that generates the stimulation energy.

Although the implantable stimulators 12 have been described as pacemakers, it should be appreciated that the implantable stimulators 12 may take the form of any device used to therapeutically stimulate body tissue using electrical energy, e.g., an implantable cardioverter defibrillator (ICD), deep brain stimulator (DBS), pain relief nerve stimulator, vagus nerve stimulator, or bladder control stimulator. It should also be appreciated that, although four implantable stimulators 12 are shown, any suitable number of implantable stimulators 12 can be used, including a single implantable stimulator 12.

Referring to FIGS. 2 and 3, the implantable stimulator 10 will now be described in greater detail. The implantable stimulator 10 generally includes a casing 22 that is composed of a biocompatible material, e.g., titanium, gold, platinum, tantalum, stainless steel, or other metal. Alternatively, other biocompatible materials may be used, e.g., a polymer, such as a fluorocarbon, polyamide, or poly ether ether ketone (PEEK), preferably covered with a metallization layer to improve the polymer's performance and/or to enhance its moisture resistance. The casing 22 is shaped such that the implantable stimulator 10 can be embedded within the tissue to be stimulated. In the illustrated embodiment, the casing 22 is bullet-shaped, i.e., it has a flat end 24 that tapers down to a pointed region 26, which can penetrate into tissue. In order to secure and stabilize the implantable stimulator 10 within the tissue, several fixation hooks 28 are mounted to the exterior of the casing 22 near the pointed region 26.

The casing 22 is substantially sealed, and preferably hermetically sealed, to isolate the components of the implantable stimulator 12 from the environment in which the implantable stimulator 10 is to be placed. The casing 22 may include one or more regions that facilitate the passage of acoustic energy through the casing 22. For example, an acoustically transparent panel 30 is suitably mounted over the exposed flat side 24 of the casing 22. Preferably, the panel 30 is a relatively thin wall of titanium or other material, e.g., having a thickness of about one half millimeter (0.5 mm) or less, that may allow the acoustic waves 20 to pass substantially therethrough.

The implantable stimulator 10 further includes an acoustic transducer array 32, a stimulation electrode 34, a reference electrode 36, and a power/communication unit 38. The stimulation electrode 34 is mounted on the pointed region 26 of the casing 22, and the reference electrode 36 is mounted on the flat side 24 of the casing 22. The stimulation electrode 34 is used to electrically stimulate adjacent tissue, and the reference electrode 36 is used as a reference. In the illustrated embodiment, the transducer array 32 comprises four acoustic transducer cells 40 (shown in phantom in FIG. 3). It should be appreciated, however, that the number of transducer cells 40 will ultimately depend on the amount of power needed to energize the implantable stimulator 10, as will be described in further detail below.

The power/communication unit 38 is coupled to the acoustic transducer array 32 and reference electrode 36 via lead 42 and coupled to the stimulation electrode 34 via lead 44 (shown partially in phantom). The power/communication unit 38 is configured for providing electrical stimulation energy to the stimulation electrode 34 in accordance with stimulation parameters stored within the implantable stimulator 12.

The implantable stimulator 12 may optionally include additional secondary stimulation electrodes (not shown), which may be coupled to the power/communication unit 38 via either separate leads, so that the power/communication unit 38 can independently transmit stimulation energy to the electrodes, or using lead 44, so that the power/communication unit 38 can transmit stimulation energy to the electrodes as a group. The implantable stimulator 12 may optionally include one or more sensors (not shown) capable of measuring physiological parameters, such as temperature, electrical impedance, pressure, position, strain, pH, fluid flow, and the like. As will be described in further detail below, this diagnostic information can be used to control the transmission of stimulation energy. Further details regarding the use of sensors and corresponding componentry is disclosed in U.S. patent application Ser. No. 09/989,912, which is expressly incorporated herein by reference.

Referring still to FIG. 2, the acoustic transducer array 32 comprises a substrate 46, four cavities 48 formed completely or partially through the substrate 46, and a flexible piezoelectric layer 50 disposed over the substrate 46 across the cavities 48. The four cavities 48 are filled with a gas, such as air, and thus, the piezoelectric layer 50 will vibrate over the cavities 48, preferably at a frequency equal to the natural frequency of the piezoelectric layer 50. In the illustrated embodiment, each cavity 48 is circular, but can also have other shapes, such as elliptical or rectangular.

The previously described reference electrode 36 is mounted to the outer surface of the piezoelectric layer 50 between the cavities 48. Thus, it can be appreciated that the reference transducer 36 serves as both a common electrode that couples the transducer cells 40 together to provide energizing electrical energy, and a reference point during electrical stimulation of the stimulation electrode 34. Alternatively, a separate common electrode or multiple electrodes (one for each transducer cell 40) can be used to provide the energizing electrical energy to the power/communication unit 38. The acoustic transducer array 32 further comprises four counter electrodes 52 (only two shown in FIG. 2) that are mounted to the inner surface of the piezoelectric layer 50 within the respective cavities 48. In the illustrated embodiment, the transducer cells 40 are connected in parallel by the common electrode 36 in order to increase the generated current. Alternatively, the transducer cells 40 can be connected in series in order to increase the generated voltage.

Thus, it can be appreciated that acoustic waves transmitted to the acoustic transducer array 32 from an external source will cause the piezoelectric layer 50 to vibrate above the cavities 48. As a result, the periodic mechanical strain exerted on the piezoelectric layer 50 generates electrical current at the common electrode 36. Similarly, as electrical current are transmitted to the acoustic transducer array 32 from the power/communication unit 38, an electrical charge will be induced in the piezoelectric layer 50, thereby causing the piezoelectric layer 50 above the cavities 48 to periodically vibrate, resulting in the transmission of acoustic waves.

As best illustrated in FIG. 2, a plurality of depressions are formed in the piezoelectric layer 50, thereby enhancing the efficiency and/or sensitivity of the acoustic transducer array 32. The depressions may also be used to tune the natural resonant frequency of the piezoelectric layer 50. The depressions can be formed by providing the cavities 48 with an internal pressure that is less than the atmospheric pressure, such that the piezoelectric layer 50 partially enters the cavities 48.

In the illustrated embodiment, the diameter of each cavity 48 is approximately 1.2 mm, which results in a maximum acoustic to electrical energy exchange at a frequency of about 40 KHz-translating to a wavelength of 4 cm in water. Since each transducer cell 40 is much smaller than this wavelength, the performance of the implantable stimulator 12 is not affected by the orientation of the transducer array 32 with respect to the acoustic waves 20 transmitted by the control device 14. Further details regarding the structure and manufacture of acoustic transducer arrays are described in U.S. Pat. No. 6,140,740, which is expressly incorporated herein by reference.

Referring now to FIG. 4, the power/communication unit 38 comprises a rectifier 54 and an energy storage device 56. The rectifier 54 is coupled to the transducer array 32 for converting the electrical current generated by the transducer array 32 into a form suitable for powering components of the implantable stimulator 12. Specifically, the rectifier 54 is configured for converting incoming alternating current (AC) voltage from the transducer array 32 into direct current (DC) voltage for storage by the energy storage device 56. The rectification may be performed by diodes arranged in a configuration suitable for the requirements of the mode of operation, preferably resulting in a passive circuit that draws substantially no current. For example, a half-bridge and full-bridge configuration can be used. Alternatively, other rectification circuits (not shown) may be used, including Schottky diodes, voltage triplers or other multiplier circuits, and the like. In addition, the rectifier 54 may include an overvoltage protector (not shown), which may prevent the energy storage device 56 from overcharging to unsafe levels. For example, the overvoltage protector may include a Zener diode, or a transistor that opens at a predetermined threshold voltage.

The energy storage device 56 is capable of being charged from an external source (such as the control device 14) using acoustic energy received by the acoustic transducer array 32. The energy storage device 56 may include any of a variety of devices, such as an energy exchanger, a battery, and/or a capacitor. Preferably, the energy storage device 56 is a battery capable of storing electrical energy substantially indefinitely unless actively discharged. In another embodiment, the energy storage device 56 may include both a capacitor and a primary, non-rechargeable battery, although, alternatively, the energy storage device 56 may include a secondary, rechargeable battery and/or capacitor that may be energized before activation or use of the implantable stimulator 12. For example, the energy storage device 56 may include a Lithium thin film battery, such as those available from Oak Ridge Micro-energy Inc. of Salt Lake City, Utah, Infinite Power Supply of Denver, Colo., or Cymber Corporation of Elk River, Minn. Alternatively, the energy storage device 56 may include a standard coin type manganese lithium rechargeable battery, such as those available from Matsushita Battery Industrial Co., Ltd. (MBI) of Osaka, Japan.

The power/communication unit 38 further comprises a controller 58 coupled between the electrodes 34 and 36 for providing electrical stimulation energy to the electrode 34. The controller 58 may include one or more controllers for controlling components of the implantable stimulator 12, timer circuitry (e.g., a clock or counter), reset and threshold circuitry, and/or a processor for generating electrical signals being transmitted by and/or analyzing electrical signals received by the transducer array 32. The controller 58 can be configured using digital signal processors (DSPs), Field Programmable Gate Arrays (FPGAs), Application Specific Integrated Circuit (ASIC)-compatible microprocessors, such as a CoolRISC processor available from Xemics, or other programmable devices, and/or any other hardware components or software modules that may be required for processing, analyzing, storing data, and controlling operation of the implantable stimulator 12.

The power/communication unit 38 further comprises signal detect circuitry 60 coupled to the transducer array 32 for providing a communication channel into the implantable stimulator 12, and specifically, to pass commands and/or information in the acoustic communication waves received by the transducer array 32 for use by the controller 58. For example, the signal detect circuitry 60 may pass commands or other signals to the controller 58, e.g., that acoustic energizing waves have been discontinued, that the implantable stimulator 12 should become operative and/or stimulation parameters. The signal detect circuitry 60 may be a passive FET circuit, thereby drawing substantially no current. The signal detect circuitry 60 may also include a smoothing capacitor (not shown) and/or logic for reducing the sensitivity of the signal detect circuitry 60 to spurious transient signals.

The power/communication unit 38 comprises optional transmission circuitry 62 coupled to the transducer array 32 for providing a communication channel from the implantable stimulator 12, e.g., to pass status information or optional sensor data to the control device 14 as acoustic communication waves. The signals are preferably digital electrical signals, which may be generated, for example, by grounding the counter electrodes 52 (shown in FIG. 2) of the transducer array 32 and alternately connecting the common electrode 36 (shown in FIG. 2) between ground and a predetermined voltage. Alternatively, the signals may be generated by alternately grounding the common electrode 36 and connecting the counter electrodes 52 to the predetermined voltage, and then grounding the counter electrodes 52 and connecting the common electrode 36 to the predetermined voltage. In a further alternative, the signal may be processed or modulated, e.g., using spread spectrum, direct sequence mixing, code division multiple access (CDMA), or other technologies, as will be appreciated by those skilled in the art.

The power/communication unit 38 comprises memory 64, e.g., volatile or non-volatile memory, including flash memory or ferroelectric memory. The memory 64 may store information, e.g., data received from the optional sensors of the implantable stimulator 12, commands and stimulation parameters for use by the controller 58 to provide stimulation energy to the electrode 34.

The power/communication unit 38 comprises a switch 66 coupled between the energy storage device 56 and the controller 58, such that all or part of the controller 58 may be selectively activated and deactivated under control of the control device 14. Optionally, use of the switch 66 may be foregone, in which case the controller 58 can be directly connected to the energy storage device 56, such that at least some component(s) of the controller 58 may remain active at all times.

The switch 66 can be operated to alternately place the implantable stimulator 12 in an "active mode" or a "dormant mode." Specifically, to place the implantable stimulator 12 in the active mode, the switch 66 may be closed upon acoustic excitation by an external acoustic energy source, e.g., from the control device 14, to allow current flow from the energy storage device 56 to the controller 58, thereby activating the implantable stimulator 12. To place the implantable stimulator 12 in a "dormant mode," the switch 66 can may be opened upon acoustic excitation by the control device 14, to prevent current from flowing from the energy storage device 56 to the controller 58. Basically, an acoustic transmission from the control device 14 may vibrate the transducer array 32, forming a voltage pulse that is conveyed to the switch 66. When the voltage exceeds a predetermined threshold, e.g., about a half volt (0.5 V), the switch 66 may close if previously in an open state, or open if previously in a closed state.

Further details regarding the structure and function of the power/communication unit 38 are disclosed in U.S. patent application Ser. No. 09/989,912, which has previously been incorporated herein by reference.

Figure 5:
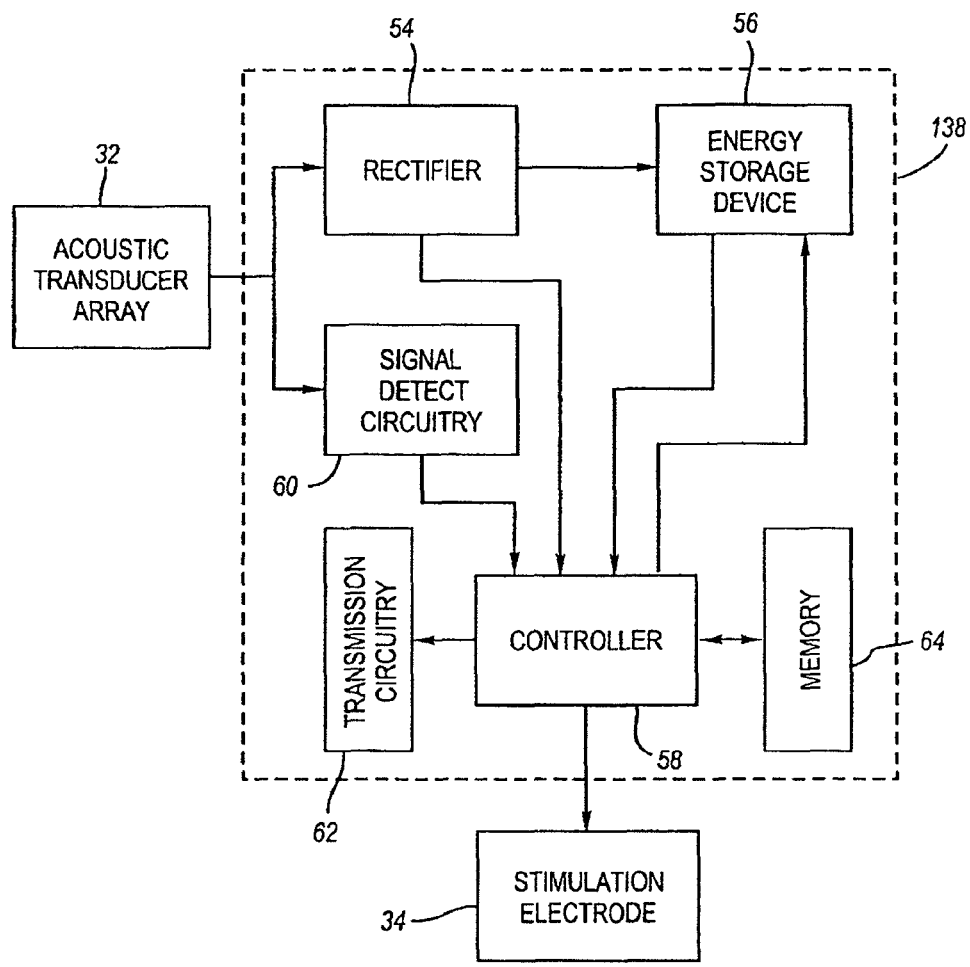
FIG. 5 is a block diagram of an alternative power/communication unit that can be used in the implantable stimulator of FIG. 2.

Referring to FIG. 5, an alternative embodiment of a power/communication unit 138 that can be used in the acoustic stimulator 12 is described. The power/communication unit 138 is similar to the power/communication unit 38 described above, with the exception that the controller 58 immediately uses the electrical current to generate the stimulation energy. Specifically, the controller 58 receives the electrical energy directly from the rectifier 54 and generates the stimulation energy in response thereto. Any excess electrical energy not used by the controller 58 to generate the stimulation energy is output to the energy storage device 56 for subsequent use by the controller 58 or other components.

The following description illustrates exemplary energy consumption parameters needed for the power/communication unit 138 to generate the proper amount of stimulation energy, and, consequently, exemplary power requirements for the acoustic transducer array 32. A single acoustic transducer cell 40 will typically generate 15 Pq/KPa at a frequency of approximately 40 KHz and a voltage of 10 V. The theoretical induced current at an acoustic pressure of 50 KPa will be 15 Pq/KPa×50 KPa×40 KHz=30 µA. Assuming a 50% AC to DC rectification efficiency, the practical induced current will be 15 µA. The resulting power will be 15 µA×10 V=0.15 mW. Assuming that twenty acoustic transducer cells 40 are connected in parallel, the total power generated by the transducer array 32 will be 20×0.15 mW=3 mW. A typical pacemaker has the following operational characteristics: amplitude of 2.5 V, frequency of 80 Hz, pulse width of 0.4 msec, and impedance of 1000 ohms. Thus, the power required by the acoustic stimulator 12 will be $(2.5 V)^2 \times 1/1000$ ohms×80 Hz×4×$10^{-4}$ sec=0.2 mW. As such, the implantable stimulator 12 (assuming 20 transducer cells 40) will generate 15 times the energy required for pacing the heart 18. The excess energy can be used to charge the energy storage device 56 to allow operation of the implantable stimulator 12 without acoustic excitation from the control device 14.

Figure 6:
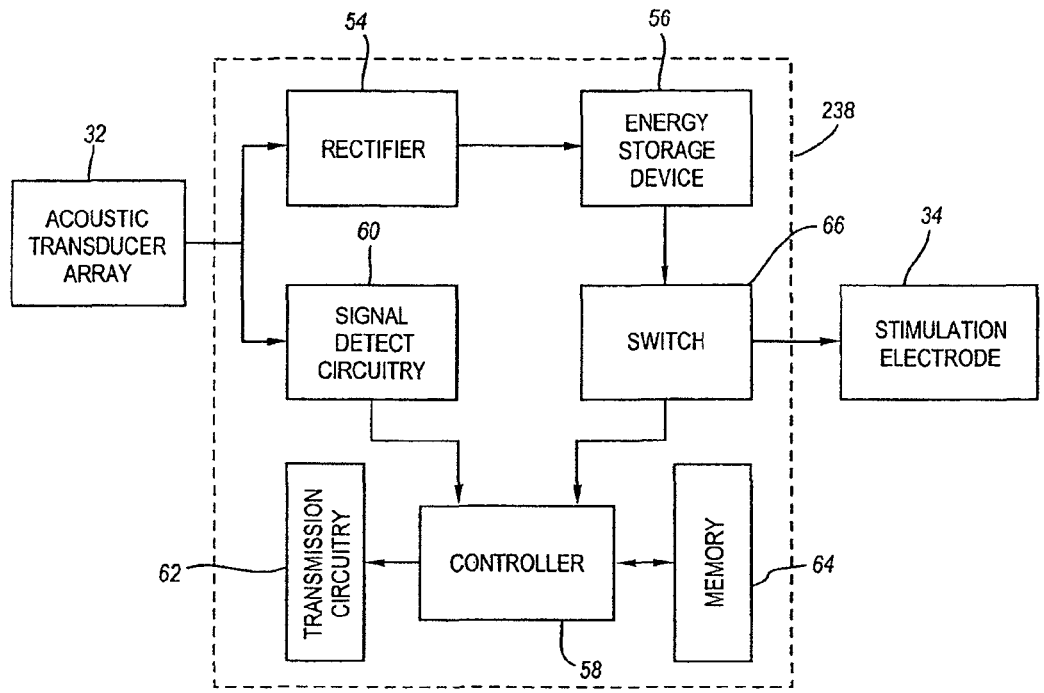
FIG. 6 is a block diagram of another alternative power/communication unit that can be used in the implantable stimulator of FIG. 2.

Referring to FIG. 6, another alternative embodiment of a power/communication unit 238 that can be used in the acoustic stimulator 12 will now be described. The power/communication unit 238 is similar to the previously described power/communication unit 38, with the exception that the controller 58 does not output the stimulation energy. Rather, the controller 58 alternately opens and closes the switch 66 in order to discharge the energy storage device 56 through the switch 66 to produce the stimulation energy. In this case, the frequency that the switch 66 is opened and closed defines the frequency of the stimulation energy, and the duration that the switch 66 is opened in each cycle defines the pulse width of the stimulation energy.

Figure 7:
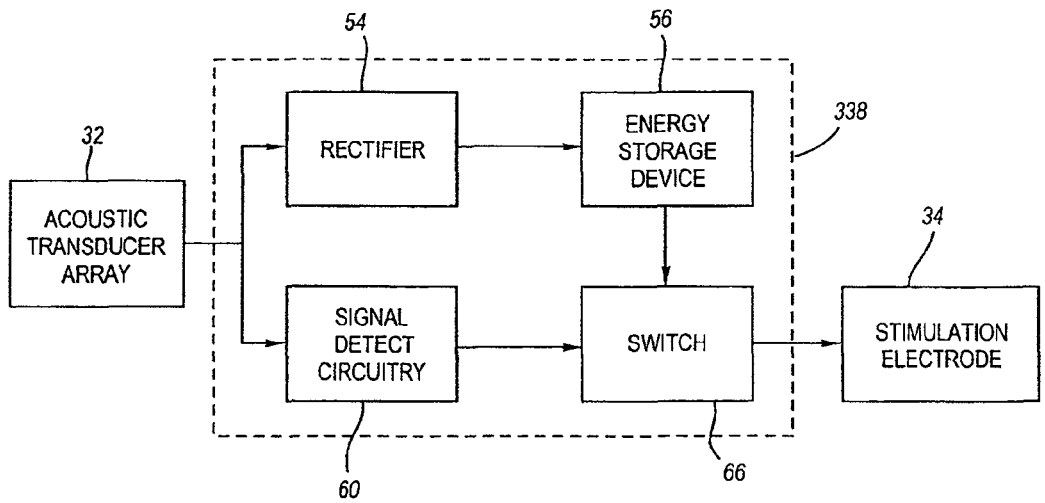
FIG. 7 is a block diagram of still another alternative power/communication unit that can be used in the implantable stimulator of FIG. 2.

Referring to FIG. 7, still another alternative embodiment of a power/communication unit 338 that can be used in the acoustic stimulator 12 will now be described. The power/communication unit 338 is similar to the previously described power/communication unit 238, with the exception that a controller 58 is not used to alternately open and close the switch 66. Instead, the control device 14 alternately opens and closes the switch 66 by transmitting acoustic communication waves 20 to the implantable stimulator 12. Because output of the stimulation energy is completely controlled by the control device 14, the power/communication unit 338 need not include a controller 58, thereby rendering the implantable stimulator 12 a "dumb device." Of course, the power/communication unit 338 can alternatively use a controller 58 if control of other functions within the implantable stimulator 12, such as sensing, is needed.

Figure 8:
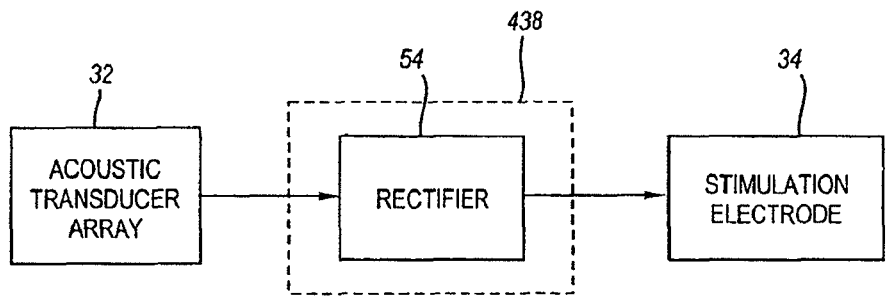
FIG. 8 is a block diagram of yet another alternative power/communication unit that can be used in the implantable stimulator of FIG. 2.

Referring to FIG. 8, yet another alternative embodiment of a power/communication unit 438 that can be used in the acoustic stimulator 12 will now be described. Like the power/communication unit 338, the power/communication unit 438 is a "dumb device." Unlike the power/communication unit 338, the output of the stimulation energy is not controlled by alternately opening and closing a switch 66. Rather, the control device 14 transmits acoustic energizing waves 20 in accordance with stimulation parameters stored in the control device 14. For example, the control device 14 can generate pulsed acoustic energizing waves 20 that is transformed into pulsed electrical energizing waves in the implantable stimulator 12. The power/communication unit 338 comprises a rectifier 54 that then transforms the AC components of the pulsed electrical current into DC components, thereby resulting in a digital electrical signal, which is then output from the implantable stimulator 12 as stimulation energy.

Figure 9:
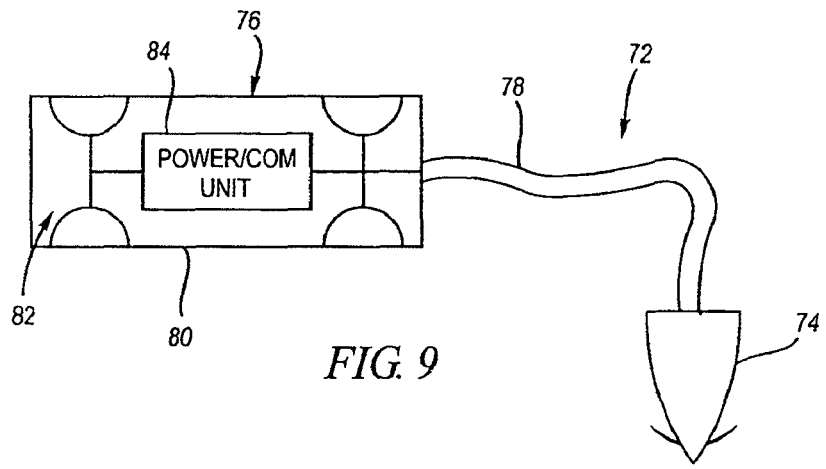
FIG. 9 is a side view of an alternative implantable stimulator that can be used in the acoustic stimulation system of FIG. 1.

Although the previously described implantable stimulator 12 is self-contained, thereby eliminating the need to implant and route external leads, other types of implantable stimulators can be used in the stimulation system 10 instead of the implantable stimulator 12. For example, FIG. 9 illustrates an alternative embodiment of an implantable stimulator 72 that uses an external lead. Specifically, the implantable stimulator 72 comprises a stimulating electrode 74 and a control unit 76 that are coupled together through an external lead 78. Alternatively, several stimulating electrodes can be provided. For example, the stimulating electrodes may be independent of each other, in which case, the electrodes can be connected to the control unit 76 via parallel external leads. Or the stimulating electrodes may be integrated together on a single unit, in which case, the electrode unit can be connected to the control unit 76 via a single external lead with one or more wires.

The control unit 76 comprises a casing 80 that is similar to the previously described casing 22, with the exception that the casing 80 is cylindrically shaped. The control unit 76 further comprises an acoustic transducer array 82 that is similar to the previously described transducer array 32, with the exception the transducer array 82 is circumferentially distributed around the cylindrical casing 80. The control unit 76 further comprises the previously described power/communication unit 84, which is suitably mounted within the casing 80. Since almost all of the componentry is located within the control unit 76, the stimulation electrode 74 can be made smaller, thereby facilitating delivery and implantation of the stimulation electrode 74 in the target region of the heart 18. The control unit 76 may be implanted in the chest region of the patient 16.

Figure 10:
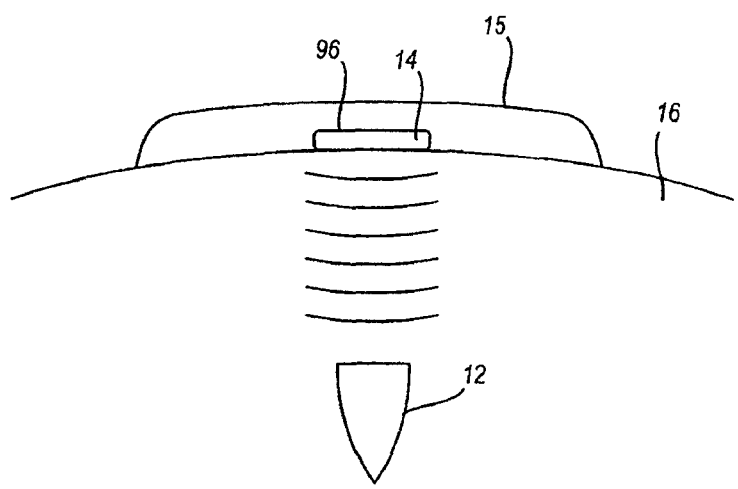
FIG. 10 is a side view of an external control device used in the acoustic stimulation system of FIG. 1.
Figure 11:
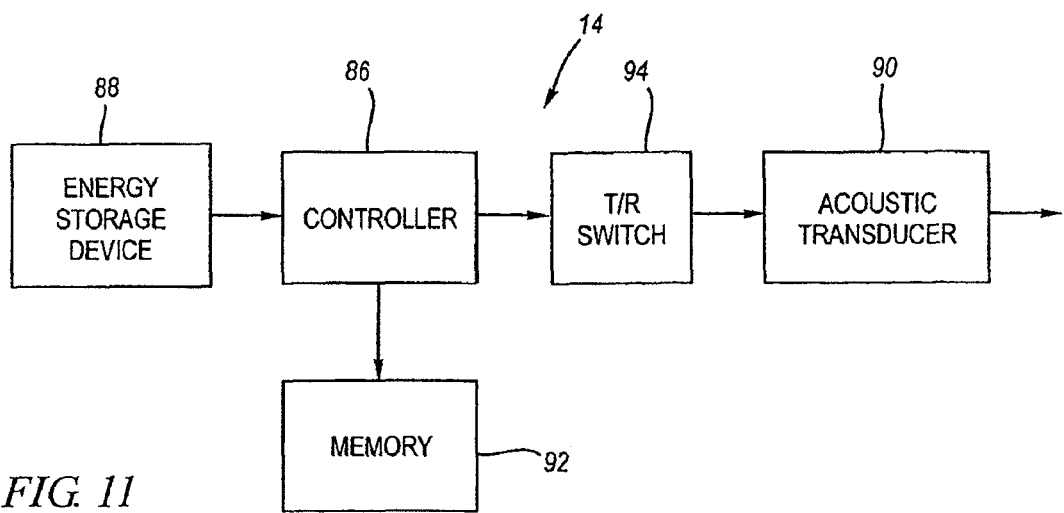
FIG. 11 is a block diagram illustrating the components of the external control device of FIG. 10.

With particular reference to FIGS. 10 and 11, the control device 14 will now be described in detail. The control device 14 comprises a controller 86 for controlling its operation, and an energy storage device 88, e.g., a nonrechargeable or a rechargeable battery, coupled to the controller 86 and/or other components of the control device 14, such as a power amplifier or an oscillator (not shown). In addition, the control device 14 comprises an acoustic transducer 90 configured for converting between electrical current and acoustic waves in a similar manner described above with respect to the transducer array 32. Alternatively, separate and/or multiple acoustic transducers may be provided for transmitting and receiving acoustic waves.

The control device 14 further comprises memory 92 coupled to the controller 86, e.g., for storing commands, stimulation parameters, and/or data provided to the control device 14, as explained further below. The memory 92 may be a temporary buffer that holds data before transfer to another device, or non-volatile memory capable of storing the data substantially indefinitely, e.g., until extracted by the controller 86. For example, the memory 92 may be a memory card or an EPROM (not shown) built into the control device 14 or otherwise coupled to the controller 86. In the preferred embodiment, the implantable stimulator 12 may be operated in a "half-duplex" mode. In this mode, the implantable stimulator 12 can only either transmit or receive during any given time. To this end, the control device 14 comprises a transmitting/receiving (T/R) switch 94, which toggles the transducer 90 to alternately transmit and receive acoustic energy. Lastly, the control device 14 comprises a casing 96 for housing the previously described components.

As best illustrated in FIG. 10, the control device 14 is preferably carried by a patch 15 that may be secured to a patient, e.g., to the patient's skin. For example, the patch 15 may include one or more layers of substantially flexible material to which the control device 14 and/or its individual components are attached. The patch 15 may include a single flexible membrane (not shown) to which the control device 14 is bonded or otherwise attached, e.g., using a substantially permanent adhesive, which may facilitate conformance of the patch 15 to the patient's anatomy. Alternatively, the control device 14 may be secured between layers of material, e.g., within a pouch or other compartment (not shown) within the patch 15. For example, the patch 15 may include a pair of membranes (not shown) defining the pouch or compartment. The space within which the control device 14 is disposed may be filled with material to acoustically couple the acoustic transducer 90 of the control device 14 to an outer surface of the patch 15. Alternatively, the acoustic transducer 90 may be exposed, e.g., in a window formed in a wall of the patch 15.

The patch 15 may be formed from a flexible piezoelectric material, such as Polyvinylidene Fluoride (PVDF) or a PVDF copolymer. Such polymers may allow the patch 15 to produce ultrasonic waves, as well as allow the control device 14 to be secured to the patient's skin. Thus, the wall of the patch 15 itself may provide an acoustic transducer for the control device 14, i.e., for transmitting acoustic energy to and/or receiving acoustic energy from the implantable stimulator 12.

The patch 15 may then be secured to the patient's skin using a material, such as a layer of adhesive (not shown), substantially permanently affixed or otherwise provided on a surface of the patch 15. The adhesive may be hydrogel, silicon, polyurethane, polyethylene, polypropylene, fluorocarbon polymer, and the like. Alternatively, a separate adhesive may be applied to the patch 15 and/or to the patient's skin before applying the patch 15 in order to secure the control device 14 to the patient's skin. Such an adhesive may enhance acoustic coupling of the acoustic transducer(s) of the control device 14 to the patient's skin, and consequently to the implantable stimulator 12. Optionally, additional wetting material, including water, silicone oil, silicone gel, hydrogel, and the like, and/or other acoustically conductive material may be provided between the patch 15 or the acoustic transducer 90, and the patient's skin, e.g., to provide substantial continuity and minimize reflection or other losses and/or to secure the patch 15 to the patient 16.

The patch 15 may be relatively light and compact, for example, having a maximum surface dimension (e.g., width or height) not more than about ten to two hundred millimeters (10-200 mm), a thickness not more than about five to one hundred millimeters (5-100 mm), and a weight not more than about twenty to four hundred grams (20-400 g), such that the control device 14 may be inconspicuously attached to the patient. Thus, the patient 16 may be able to resume normal physical activity, without substantial impairment from the control device 14. Yet, the energy storage device 88 may be sufficiently large to communicate with the implantable stimulator 12 for an extended period of time, e.g., for hours or days, without requiring recharging or continuous coupling to a separate energy source.

Alternatively, the control device 14 may be carried by a belt (not shown) that may be secured around the patient, e.g., such that the acoustic transducer 90 is secured against the patient's skin. The belt may carry other components, e.g., an external power supply for the control device 14. For example, a battery pack (not shown) may be carried by the belt that may be coupled to the control device 14 for providing electrical energy for its operation. Alternatively, the control device 14 may take the form of a probe that is not worn by the patient 16, but rather can be selectively placed on the chest in order to communicate with the implantable stimulator 16.

Figure 12:
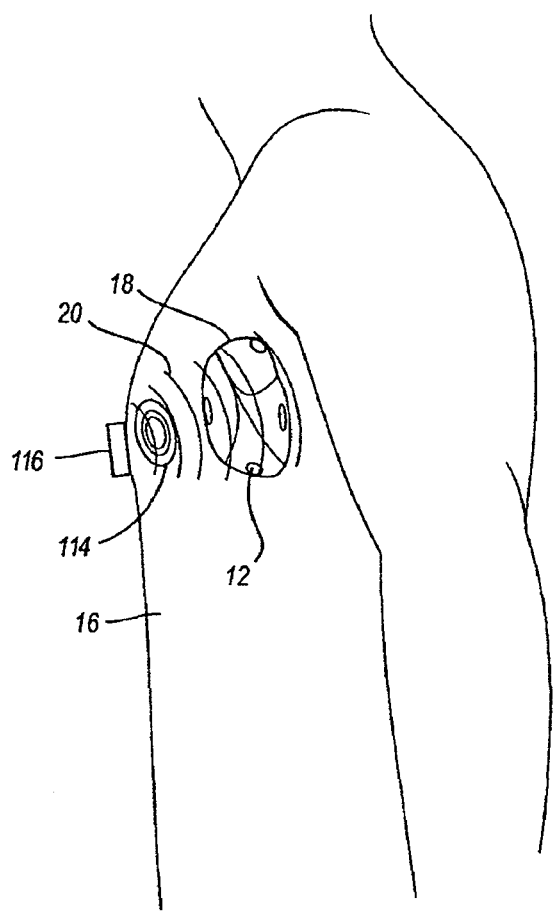
FIG. 12 is a side view showing the use of an alternative implantable control device used to control implantable stimulators within a patient.

Alternatively, a control device, similar to the previously described control device 14, may be implanted within the patient 16, e.g., the chest near the heart region. For example, FIG. 12 illustrates an implantable control device 114 that can be used to communicate with an implantable stimulator 16 within the heart 18 of the patient 16. In this case, the implantable control device 114 communicates in the same manner as the control device 14. The main difference is that the implantable control device 114 is preferably capable of being recharged by an external energizing device 116 via RF or acoustic energy. In addition, the implantable control device 114 will typically not have the required stored energy for energizing the implantable stimulators 16. Instead, the implantable stimulators 16 may be energized by the external energizing device 116. In this case, the implantable control device 114 will be used to control the operation of the implantable stimulators 16, e.g., by alternately activating and deactivating selected implantable stimulators 16, or otherwise controlling the stimulation energy output from the implantable stimulators 16. Further details on this particular arrangement are disclosed in U.S. patent application Ser. No. 10/413,428, which is expressly incorporated herein by reference.

When used in conjunction with the implantable stimulator 12 having the power/communication unit 36 or power/communication unit 236 illustrated in respective FIGS. 4 and 6, the control device 14 can be operated in an "energizing mode" or "activation mode." When operated in either of these modes, the control device 14 transmits acoustic waves 20 from the acoustic transducer 90 through the body of the patient 16, with at least a portion of the acoustic waves 20 striking the transducer array 32 of the implantable stimulator 12. The transducer array 32 converts the acoustic waves into electrical current, which are used to either charge the energy storage device 56 or communicate with the controller 86 in the implantable stimulator 12 depending on the operational mode.

At the beginning of the energizing mode, the control device 14 determines the optimum frequency at which the implantable stimulator 12 should be energized. For example, the control device 14 may transmit broadband acoustic waves or scanning waves, i.e., scanning through a range of frequencies, and wait for the implantable stimulator 12 to respond. The implantable stimulator 12 may transmit acoustic waves at different frequencies in response to the diagnostic signal, and the control device 14 may determine the optimal frequency for communicating with the implantable stimulator 12 based upon the responses. For example, the control device 14 may repeatedly charge the implantable stimulator 12 using different frequency signals and measure the length of time that the implantable stimulator 12 is capable of transmitting data signals at each frequency to determine the optimal frequency. Alternatively, when the implantable stimulator 12 detects the signal, it may transmit a response at an optimal frequency that should be used to communicate with the implantable stimulator 12.

Once the control device 14 has determined the optimal frequency for communicating with the implantable stimulator 12 (or the control device 14 may already know the proper frequency to use), the control device 14 then transmits acoustic energizing waves 20 to the implantable stimulator 12, which are transformed and stored in the energy storage device 56 as electrical energy. The energy storage device 56 continues to store electrical energy until a predetermined voltage is achieved, e.g., about eight Volts (8 V), and then the controller 58 automatically disconnects the energy storage device 56 from the transducer array 32. After a predetermined time, e.g., between about five and sixty seconds (5-60 sec.), the control device 14 automatically ceases the energizing transmission. Alternatively, the control device 14 may cease energizing the implantable stimulator 12 by transmitting a stop command.

During the activation mode, the control device 14 transmits a command to the implantable stimulator 12 to close the switch 66, thereby placing the implantable stimulator 12 in the active mode. Once activated, the implantable stimulator 12 draws electrical energy from the energy storage device 56, and begins to transmit electrical energy to the stimulation electrode 34 in accordance with stimulation parameters, which may be previously stored in the memory 92 or may be transmitted from the control device 14 immediately after activation of the implantable stimulator 12. Alternatively, if no switch 66 is used, the control device 14 may transmit a start command to the implantable stimulator 12, which responds by transmitting electrical energy to the stimulation electrode 34.

The implantable stimulator 12 continues to stimulate the tissue until the control device 14 transmits a command to the implantable stimulator 12 to open the switch 66, thereby deactivating the implantable stimulator 12 and placing it in the dormant mode. Alternatively, if no switch 66 is used, the control device 14 may transmit a stop command to the implantable stimulator 12, which responds by ceasing transmission of the electrical energy to the stimulation electrode 34. Stimulation may also cease if the voltage of the energy storage device 56 falls below a predetermined threshold, e.g., below a level at which the stimulation electrode 34 may not continue to operate effectively, such as 1.5 volts. After the voltage falls below the predetermined threshold, the controller 58 may automatically discontinue operation of the implantable stimulator 12 by opening the switch 66 and returning to a dormant state until energized and activated by the control device 14.

Prior to, during, or subsequent to the activation mode, the control device 14 and implantable stimulator 12 may communicate additional information to each other. For example, the implantable stimulator 12 may transmit diagnostic information, which has been sensed by the optional sensor (not shown), to the control device 14. The control device 14 can then use this information to control the operation of the implantable stimulator 12. For example, the optional sensor can be a pressure sensor that can sense the blood flow through the heart chamber in which the implantable stimulator 12 is located. In this case, the implantable stimulator 12 can transmit pressure information to the control device 14. Alternatively, the pressure sensor may be even associated with another implantable device that is located in another region of the body, e.g., a pulmonary vein. The control device 14 may then respond to this pressure information by either activating or deactivating the implantable stimulator 12.

For example, if the pressure information indicates that the blood flow is below normal, the control device 14 may activate the implantable stimulator 12 by transmitting commands to close the switch 66, thereby initiating stimulation of the heart tissue. Once the diagnostic information indicates that the blood flow has been normal for a predetermined period of time, the control device 14 can then deactivate the implantable stimulator 12 by transmitting commands to open the switch 66, thereby ceasing stimulation of the heart tissue. This technique lends itself well to implantable cardioverter defibrillators (ICDs), which are designed to shock the heart when the blood pressure within the heart falls to a dangerous level. The control device 14 may alternatively or optionally use the diagnostic information to control the implantable stimulator 12 by controlling the parameters of the stimulation energy output by the implantable stimulator 12.

As another example for communicating information to each other, the control device 14 may transmit an identification code when transmitting commands to open or close the switch 66 in the implantable stimulator 12. In this manner, timing and sequence of the stimulation energy output from all of the implantable stimulators 12 can be controlled. Prior to placing the implantable stimulator 12 in the dormant mode, the controller 58 may transmit status information to the control device 14, e.g., an initial confirmation of instructions received from the control device 14, an identification code identifying the implantable stimulator 12, and/or a stop notice when stimulation is being discontinued by the controller 58.

As a safety measure against false positives (e.g., erroneous activation or deactivation), the control device 14 may acoustically transmit an initiation signal followed by a confirmation signal. When the implantable stimulator 12 receives these signals, the controller 58 may monitor the signals for a proper sequence, thereby ensuring that the switch 66 only closes upon receiving the proper initiation and confirmation signals. For example, the controller 58 may only acknowledge an activation signal that includes a first pulse followed by a second pulse separated by a predetermined delay. Use of a confirmation signal may be particularly important for certain applications, for example, to prevent unintentional stimulation of the heart 18.

In the case where the power/communication unit 138 illustrated in FIG. 5 is used in the implantable stimulator 12, the electrical current transformed by the implantable stimulator 12 is not used to charge the energy storage device 56, but rather to immediately generate stimulation energy. As such, the control device 14 is operated in the energizing mode in order to energize the implantable stimulator 12, resulting in immediate output of the stimulation energy to the tissue. Communication between the implantable stimulator 12 and control device 14 can be accomplished in the same manner previously discussed above.

In the case where the power/communication unit 238 illustrated in FIG. 7 is used in the implantable stimulator 12, the control device 14 can be designed to operate in the previously described "energizing mode" and a "stimulation mode." In the energizing mode, the control device 14 energizes the implantable stimulator 12 in the same manner described above. In the stimulation mode, the control device 14 transmits acoustic communication waves to the implantable stimulator 12 in order to alternately open and close the switch 66, so that energy storage device 56 is periodically discharged to generate and output the stimulation energy, In the case where the power/communication unit 338 illustrated in FIG. 8 is used in the implantable stimulator 12, the control device 14 can be designed to operate in the energizing mode. In this case, the control device 14 transmits pulsed acoustic energizing waves in accordance with stimulation parameters stored in the control device 14. The implantable stimulator 12 responds by transforming the AC components of the resulting electrical current into DC components. That is, the pulsed AC electrical current are transformed into pulses DC electrical current, which are then output as the stimulation energy.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims

What is claimed is:

1. A stimulation system, comprising:
   a control device configured for transmitting acoustic waves through body tissue; and
   an implantable stimulator including one or more acoustic transducers configured for transforming the acoustic waves into electrical current, a power unit configured to receive the electrical current directly from the one or more acoustic transducers and to directly transform the electrical current into electrical stimulation energy, and a stimulator electrode configured for electrically stimulating adjacent body tissue using the stimulation energy.

2. The stimulation system of claim 1, the implantable stimulator further comprising a control unit operable to control the delivery of electrical stimulation energy to the stimulator electrode based at least in part on one or more stimulation parameters.

3. The stimulation system of claim 2, wherein the one or more stimulation parameters are acoustically transmitted to the implantable stimulator from the control device.

4. The stimulation system of claim 1, wherein the implantable stimulator further includes a reference electrode.

5. The stimulation system of claim 1, wherein the implantable stimulator further includes an energy storage device configured for storing a portion of the electrical current.

6. The stimulation system of claim 5, further comprising a switch configured to selectively output the electrical current from the energy storage device to alternatively activate or deactivate the implantable stimulator.

7. The stimulation system of claim 1, further comprising an external energizing device configured for charging the implantable stimulator using RF or acoustic energy.

8. The stimulation system of claim 1, wherein the power unit includes a rectifier configured to transform AC components of the electrical current into DC components of the electrical current, and the stimulator electrode is configured for electrically stimulating adjacent body tissue using the DC components of the electrical current as electrical stimulation energy.

* * * * *